United States Patent [19]

Madon

[11] Patent Number: 4,477,595
[45] Date of Patent: Oct. 16, 1984

[54] LIQUID HYDROCARBON SYNTHESIS USING SUPPORTED RUTHENIUM CATALYSTS

[75] Inventor: Rostam J. Madon, Scotch Plains, N.J.

[73] Assignee: Exxon Research and Engineering Co., Florham Park, N.J.

[21] Appl. No.: 489,562

[22] Filed: Apr. 28, 1983

Related U.S. Application Data

[63] Continuation of Ser. No. 363,951, Mar. 31, 1982, abandoned, which is a continuation of Ser. No. 264,426, May 18, 1981, abandoned.

[51] Int. Cl.$^3$ .............................................. C07C 1/04
[52] U.S. Cl. ................................................... 518/715
[58] Field of Search ......................................... 518/715

[56] References Cited

U.S. PATENT DOCUMENTS

| | | |
|---|---|---|
| 2,632,014 | 3/1953 | Gresham . |
| 3,922,235 | 11/1975 | DeLuca et al. . |
| 4,042,614 | 8/1977 | Vannice et al. . |
| 4,171,320 | 10/1979 | Vannice et al. . |
| 4,199,522 | 4/1980 | Murchison et al. . |

FOREIGN PATENT DOCUMENTS

| | | |
|---|---|---|
| 2712909 | 10/1977 | Fed. Rep. of Germany . |
| 2024246 | 1/1980 | United Kingdom . |

OTHER PUBLICATIONS

Dry, Advances in Fischer-Tropsch Chemistry, Ind. Eng. Chem. Prod. Res. Dev., vol. 15, No. 4, 1976, pp. 282–286.
Karn et al., I & EC Product Res. & Dev., 4, 265, (1965).
Pichler, Brenns-Chemie, 19, 226, (1938).
Pichler et al., Brenns-Chemie, 21, 247, 273, 285, (1940).
Vannice et al., III, Talk entitled, "The Difference of the Support in CO Hydrogenation Reactions", Jun. 1980.
Kugler, Talk entitled, "Synthesis of Light Olefins from CO and H$_2$", Aug. 24–29, (1980).
J. Am. Chem. Soc., 99, (8), pp. 2796–2797.
J. of Catalysis, vol. 37, pp. 449–461, (1975), "The Catalytic Synthesis of Hydrocarbons from H$_2$/CO Mixtures Over the Group VIII Metals", by M. A. Vannice.
J. of Catalysis, 63, pp. 255–260, (1980), "The Influence of the Support in the Catalytic Behavior of Ruthenium in CO/H$_2$ Synthesis Reactions", by M. A. Vannice and R. C. Garten.
"The Influence of Support on K Promotion of Ru for the Fischer–Tropsch Synthesis", by C. H. Yang et al., in ACS Div. Fuel Chem., Preprint 27, vol. 3–4, 189th ACS Nat'l Mtg., Kansas City, 1982.
"C$_1$ Chemistry/Hyrogenation of Carbon Monoxide on Supported Ruthenium Catalysts", by T. Fukushima et al., in Nippon Kagaku Kaish.
J. of Catalysis, vol. 56, pp. 236–248, (1979), "Metal–Support Effects on the Activity and Selectivity of Ni Catalysts in CO/H$_2$ Synthesis Reactions", by M. A. Vannice and R. L. Garten.
Support Effects in the Ruthenium–Catalyzed Hydroformylation of Carbon Monoxide, by S. R. Morris et al., in the publication "Metal–Support and Metal–Additive Effects in Catalysis", pp. 247–254.

*Primary Examiner*—Howard T. Mars
*Attorney, Agent, or Firm*—Robert J. North; Edward H. Mazer

[57] ABSTRACT

Selective production of C$_5$–C$_{40}$ hydrocarbons containing C$_5$–C$_{20}$ hydrocarbons having a high paraffins content, i.e., for producing gasoline and diesel fuel and useful as a chemical feedstock, is achieved by contacting H$_2$/CO mixtures with supported ruthenium catalysts under conditions including elevated temperature and ratios of gas hourly space velocity/pressure below about 24,000 v/v/hr/MPaA to effect percent CO conversions at least about 20%. The ruthenium catalyst support contains a titanium oxide, niobium oxide, vanadium oxide or tantalum oxide and C$_5$–C$_{40}$ hydrocarbons can be selectively obtained in about 60–90 weight percent of total hydrocarbon products.

15 Claims, No Drawings

LIQUID HYDROCARBON SYNTHESIS USING SUPPORTED RUTHENIUM CATALYSTS

This is a continuation of application Ser. No. 363,951 filed Feb. 31, 1982 which is a Rule 60 continuation of Ser. No. 264,426 filed May 18, 1981, both now abandoned.

BACKGROUND OF THE INVENTION

This invention relates to a process for producing $C_5$-$C_{40}$ hydrocarbons having a high paraffins content wherein mixtures of $H_2$/CO are contacted with supported ruthenium catalysts under process conditions to effect at least about a 20% CO conversion to hydrocarbon products.

The Fischer-Tropsch (F-T) synthesis reaction is well-known for producing a variety of hydrocarbon and oxygenated products by contacting $H_2$/CO mixtures with a heterogeneous catalyst, usually iron-based, under conditions of elevated temperature and pressure. The range of gaseous, liquid and solid hydrocarbon products that can be obtained include methane, $C_2$-$C_4$ paraffins, gasoline motor fuel, diesel motor fuel and reforming fractions, heavy hydrocarbon waxes, and olefins. Hydrocarbon fractions which are enormously important, in light of the current world energy crisis, are the diesel motor fuel and motor gasoline cut, i.e., $C_5$-$C_{20}$ hydrocarbons, and the $C_{21}$-$C_{40}$ cut, which can be steam-cracked to yield light olefin feedstocks.

A commercial F-T operation conducted by SASOL is currently in operation in South Africa in combination with a coal gasification process. Gasoline and diesel motor fuel are produced by contacting $H_2$/CO mixtures between 150°-300° C. and 20-25 atmospheres with iron-based catalysts.

There is a constant search for new and improved catalysts and/or processes in F-T technology which will selectively yield the $C_5$-$C_{40}$ hydrocarbon fraction, in higher yield, purity and conversion, and especially under process conditions which produce only small amounts of methane, i.e., a low methane-make.

Ruthenium catalysts are known to be active catalysts in F-T synthesis. It was discovered by Pichler (see H. Pichler, Brennstoff-Chem. 19, 226 (1938) and H. Pichler and H. Bufflet, Brennstoff-Chem. 21, 247, 273, 285 (1940) that Ru catalyst can produce from $H_2$/CO mixtures at low temperature and high pressures, very high molecular weight waxes of about MW 1000 and above, i.e., polymethylenes, having melting points of 100° C. and above.

The reference, *I&EC Product Res. & Devel.* 4, 265 (1965) by F. S. Karn et al, describes the reactivity of ruthenium on alumina catalysts in producing hydrocarbons ranging from $C_1$-$C_{30}^+$. Illustrated are runs made at 21.4 atmospheres pressure, 300/hr. space velocity, temperature of 220°-240° C. and $H_2$/CO molar ratios of 1 to 4 resulting in % CO conversions of 46-82%.

U.K. patent application No. 2,024,246A describes a hydrocarbon synthesis process for hydrocarbons in the $C_5$-$C_{12}$ range, in which mixtures of $H_2$/CO are contacted with a supported ruthenium catalyst, preferably on alumina at elevated temperature. A criticality of the process is described wherein the outlet CO partial pressure must be not less than 0.8 atmospheres at a process temperature of about 500°-525° K. and not less than 3.0 atmospheres in the temperature range of 525°-550° K.

In addition, there is described in the article, *J. of Catalysis* 57, pp. 183-186 (1979) selective $C_5$-$C_{20}$ hydrocarbon production in Fischer-Tropsch processes utilizing ruthenium on alumina catalyst.

SUMMARY OF THE INVENTION

It has now been found that paraffins are selectively produced by a process comprising:

(a) first contacting a mixture of $H_2$ and CO for at least 10 hours with a reduced and supported ruthenium catalyst under Fischer-Tropsch (F-T) conditions; and (b) continuing said contacting as in step (a) at a $H_2$/CO molar ratio from about 0.1 to 4 and thereafter recovering a hydrocarbon mixture comprising $C_5$-$C_{40}$ hydrocarbons containing $C_5$-$C_{20}$ paraffins and olefins in a paraffins to olefins weight ratio of at least about 1.5.

Also, by providing the conditions of the F-T process within specific ranges of temperature, pressure, $H_2$/CO molar ratio, gas hourly space velocity and keeping within certain space velocity/pressure relationships, at least about a 20% CO conversion can be achieved resulting in desired $C_5$-$C_{40}$ hydrocarbons. In this process, % CO conversions can normally be obtained in about 50% and higher resulting in high yields and selectivities of $C_5$-$C_{40}$ hydrocarbons.

Supported ruthenium catalysts which are operable in the process of the invention include those containing titania, vanadia, niobia, tantala, mixtures thereof, and various combinations with other co-supports. The catalysts contain 0.1 to 15 percent by weight of ruthenium, and preferably 0.1 to 5 weight percent ruthenium. Preferred catalysts in the process are Ru/$TiO_2$, Ru/$Nb_2O_5$, Ru/$V_2O_3$ and Ru/$Ta_2O_5$ and particularly Ru/$TiO_2$ and Ru/$Nb_2O_5$.

The process is conducted under a specific range of Fischer-Tropsch process conditions, i.e., temperature ranging from 100°-400° C., $H_2$/CO molar ratio of 0.1 to 4, gas hourly space velocity, (GHSV) of 100 to 50,000 v/v/hr. and a pressure of about 0.2 to 10 MPaA. The variables are chosen within these ranges such that the GHSV/pressure ratio is below 24,000 v/v/hr/MPaA and that at least about a 20% CO conversion is effected in which a 60-90 weight percent of $C_5$-$C_{40}$ hydrocarbons can be obtained of total hydrocarbons produced. At least 50 weight percent, and generally about 60 weight percent and higher of said $C_5$-$C_{20}$ fractions, are paraffins. Methane is produced up to about 15 weight percent and preferably up to 10 weight percent of the total hydrocarbons. A significant quantity of $C_{21}$-$C_{40}$ hydrocarbons is also produced which is applicable in reforming operations to yield gasoline and diesel motor fuel, and in steam cracking to yield light olefins.

Accordingly $C_5$-$C_{40}$ hydrocarbons, containing $C_5$-$C_{20}$ paraffins and olefins in a paraffins/olefins weight ratio of at least about 1.5, are produced by the process comprising (a) first contacting a mixture of $H_2$ and CO for at least 10 hours with a reduced and supported ruthenium catalyst comprising ruthenium on a support selected from the group consisting of $TiO_2$, $ZrTiO_4$, $TiO_2$-carbon, $TiO_2$-$Al_2O_3$, $TiO_2$-$SiO_2$, alkaline earth titanates, alkali titanates, rare earth titanates, $V_2O_3$, $Nb_2O_5$, $Ta_2O_5$, $Al_2O_3$-$V_2O_3$, $Al_2O_3$-$Nb_2O_5$, $Al_2O_3$-$Ta_2O_5$, $SiO_2$-$V_2O_3$, $SiO_2$-$Nb_2O_5$, $SiO_2$-$Ta_2O_5$, $V_2O_3$-carbon, $Nb_2O_5$-carbon, $Ta_2O_5$-carbon, alkaline earth-Group VB oxides, alkali-Group VB oxides, rare earth-Group VB oxides, Group IVB-Group VB oxides, and mixtures thereof, at a temperature in the range of about 100°-400° C., a pressure in the range of about 0.2 to 10 MPaA and a gas hourly space velocity, GHSV, of about 100 to 50,000 v/v/hr., wherein the ratio of GHSV/pressure is below about 24,000 v/v/hr/MPaA and the % CO conversion is at least about 20%; and (b) continuing said contacting as in step (a) at a $H_2/CO$ molar ratio from about 0.1 to 4 and thereafter recovering a hydrocarbon mixture comprising $C_5-C_{40}$ hydrocarbons containing $C_5-C_{20}$ paraffins and olefins in a paraffins to olefins weight ratio of at least about 1.5.

DESCRIPTION OF THE INVENTION AND PREFERRED EMBODIMENTS

This invention is based on the discovery that $C_5-C_{40}$ which typically contain $C_5-C_{20}$ hydrocarbons having a high paraffins content, can be selectively produced in an F-T process under a specific range of conditions including low methane make, using particular reduced and supported ruthenium catalysts that have been contacted with $H_2$ and CO under specific Fischer-Tropsch conditions for at least 10 hours. It has been found that by use of a combination of pressure, temperature, $H_2/CO$ ratio, and gas hourly space velocity within specific ranges to achieve at least about a 20% CO conversion, $C_5-C_{40}$ hydrocarbons can be selectively obtained in high yield.

Further, it has been found that the supported ruthenium catalysts described herein are more active in F-T processes than $Ru/Al_2O_3$ catalysts described hereinabove since, in general, they are able to produce similar % CO conversions at comparably lower pressures.

By the term "% CO conversion", as used herein, is meant % CO conversion per pass of total CO in the feedstream contacting the catalyst, as contrasted to total conversion including subsequent recycle of unreacted starting materials. The term, % CO conversion, per pass applies equally to a batch process as well as to a continuous one. In the process, a 50% CO conversion is preferably obtained for producing high yields of desired $C_5-C_{20}$ hydrocarbons.

The subject process variables include a $H_2/CO$ molar ratio of about 0.1 to 4 and preferably about 1 to 3. Higher molar ratios tend to produce undesirably large amounts of methane and lighter products, and lower molar ratios tend to decrease the % CO conversion under otherwise similar conditions. exhibit unexpected suppressed hydrogen and carbon monoxide chemisorption properties at room temperature. Operable catalysts in the process are preferably of the SMSI type and comprised of a support selected from the group consisting of $TiO_2$, $ZrTiO_2$, $TiO_2$-carbon, $TiO_2-Al_2O_3$, $TiO_2$-$SiO_2$, alkaline earth titanates, alkali titanates, rare earth titanates, $V_2O_3$, $Nb_2O_5$, $Ta_2O_5$, $Al_2O_3-V_2O_3$, $Al_2O_3$-$Nb_2O_5$, $Al_2O_3-Ta_2O_5$, $SiO_2-V_2O_3$, $SiO_2-Nb_2O_5$, $SiO_2$-$Ta_2O_5$, $V_2O_3$-carbon, $Nb_2O_5$-carbon, $Ta_2O_5$-carbon, alkaline earth-Group VB oxides, alkali-Group VB oxides, rare earth-Group VB oxides, Group IVB-Group VB oxides, and mixtures thereof. Preferred catalysts in the process are $Ru/TiO_2$, $Ru/Nb_2O_5$, $Ru/V_2O_3$ and $Ru/Ta_2O_5$, and particularly, $Ru/TiO_2$ and $Ru/Nb_2O_5$. By the term "$TiO_2-Al_2O_3$, $TiO_2-SiO_2$", and the like, is meant to include physical and chemical admixtures of two or more compounds, including solid solutions of two or more components forming a new compound, which may exhibit different properties from the admixture. By the term "alkali titanate, alkali earth titanate and rare earth titanate" is meant a mixture or new composition formed from $TiO_2$ and an alkali metal oxide, alkaline earth oxide or rare earth oxide, respectively.

Preferably, the catalyst is not air calcined at high temperature since it was observed in one instance that calcining unexplainedly tended to reduce the catalytic activity and % CO conversion in the subject process, of a catalyst that had been on stream for several hours.

As described hereinabove, methods of synthesizing the supported ruthenium catalyst, plus pretreatment/reduction procedures, temperature and the like, and catalytic activity are described and disclosed in U.S. Pat. Nos. 4,149,998, 3,922,235, 4,042,614 and 4,171,320 incorporated herein by reference for these purposes. Preferably, the catalyst in the subject process is subjected, as a final step before use, to a hydrogen-containing atmosphere at a temperature of at least about 200° C., and preferably about 400° C. and higher, thereby resulting in said catalyst exhibiting suppressed hydrogen chemisorption at room temperature.

The concentration of ruthenium metal in the catalyst is about 0.01 to 15% by weight of the total weight and preferably about 0.1 to 5.0 weight percent, and particularly preferred, of about 0.5 to 5 weight percent.

The products of the process include a substantial amount of $C_5-C_{40}$ chain length inclusive hydrocarbons being paraffins and olefins, being linear or branched, or mixtures thereof, and alpha or internal olefins, or mixtures thereof, and preferably linear in the product slate. In general, the $C_5-C_{40}$ hydrocarbon fraction is the largest carbon number fraction obtained in the total hydrocarbon product being at least about 60 and up to 90 weight percent of the total hydrocarbons produced, as measured on a $CO_2$-free basis.

Within the $C_5-C_{40}$ fraction, the $C_5-C_{20}$ cut represents the largest and most important hydrocarbon fraction being the gasoline and diesel motor fuel cut. Preferably, the total hydrocarbon products of the process contain at least 50 weight percent or greater of $C_5-C_{20}$ hydrocarbons, in which the $C_5-C_{20}$ paraffins/olefins weight ratio is at least 1.5 and preferably 1.8 and higher. By the term "$C_5-C_{20}$ paraffins and olefins," as used herein, is meant paraffins and olefins within the $C_5-C_{20}$ carbon number range and does not require each carbon number in the range to necessarily be present. The types of paraffins and olefins are described hereinabove. Again, the above weight percentages are measured on a $CO_2$-free weight basis.

In addition, the amount of methane produced in the subject process is up to about 15 weight percent of total hydrocarbons produced and preferably up to 10 weight percent of the total hydrocarbons produced.

The process, in general, is conducted by contacting a mixture of $H_2$ and CO with a supported ruthenium catalyst under the conditions described herein to effect at least about a 20% CO conversion to yield desired $C_5-C_{40}$ hydrocarbons and to avoid a high methane make. The combination of process variables: pressure, temperature, $H_2/CO$ molar ratio and GHSV and GHSV/pressure ratio needed to produce $C_5-C_{40}$, hydrocarbons with high selectivity cannot be defined with exactitude for a broad range of operating conditions since there will be variations in the type and scale of apparatus used, specific catalysts employed, and constraints imposed upon the process in one situation which may not be identically present in another situation. It is believed, however, that within the narrow ranges of process variables given above, and the further limitation of requiring a 20% or higher CO conversion, the selective synthesis of $C_5-C_{40}$ hydrocarbons with attendant low methane make, can be obtained. Further, it will be obvious to one skilled in the art as to how to obtain substantial yields of $C_5$–$C_{40}$ hydrocarbons in the subject process from a reading of this disclosure without an undue amount of experimentation.

Within the process variable ranges described above, several guidelines are present: generally, one initially chooses a desired $H_2/CO$ molar ratio to work with, within a 0.1 to 4 ratio, and then suitable temperature, pressure and a convenient space velocity values, which can readily be accommodated by the specific apparatus employed, and keeping within the GHSV/pressure limitation described herein. If the resulting % CO conversion of the run is below 20%, then the space velocity can be decreased, as a first step, and the pressure and/or temperature increased, as a second step, to increase the % CO conversion.

If the process, under the chosen variables, is generating too much methane or lower molecular weight hydrocarbons, then an increase in the pressure, and/or a decrease in the temperature, will serve to increase the molecular weight of the hydrocarbons into the $C_5$–$C_{40}$ range. In addition, the amount of methane make can be further reduced by decreasing the $H_2/CO$ ratio.

Conversely, if the process is producing an extensive amount of heavy hydrocarbons or heavy waxes, then a decrease in the pressure, alone, and/or increase in the temperature, will serve to decrease the molecular weight distribution down into the desired $C_5$–$C_{40}$ hydrocarbon range by controlling the process variables to achieve at least about a 20% CO conversion or higher.

In general, higher space velocity in the subject process is desirable since it optimizes the catalyst performance by maximizing feed throughput/time. However, generally, increasing the space velocity while holding the other variables constant tends to increase the olefin content of the $C_5$–$C_{40}$ hydrocarbon fraction and particularly in the lower carbon numbers of the fraction.

The product hydrocarbons can be collected out of the product stream by conventional methods including, for example, condensing heavy hydrocarbons first, then liquid condensates, then gaseous hydrocarbons. Each fraction can be analyzed by chromatography, qualitatively and quantitatively, versus known standards. The liquid condensates can be further purified by distillation to yield a $C_5$–$C_{20}$ hydrocarbon rich cut for direct use as a gasoline-base stock or diesel motor fuel base-stock.

Apparatus for carrying out the subject process are conventional in the art and include down-flow, up-flow, fixed bed, moving bed, slurry catalyst configurations and the like.

It is to be understood that obvious modifications and obvious improvements over the process described are not specifically included herein, are considered also to be within the scope of the instant invention.

Further, it is to be understood that the following Examples illustrate and set forth the best mode of carrying out the subject invention as contemplated by the inventor and should not be considered to be limitations on the scope and spirit of the instant invention.

General Description of the Process and Apparatus

The reactor used was a stainless steel vertical down-flow reactor of 0.77 cm. I.D. and 122 cm. length heated by an Alonized copper furnace.

Mixtures of CO and $H_2$ were blended with the aid of flow control valves and fed into the reactor heated at the desired temperature as controlled by Eurotherm ™ solid state controllers. Thermocouples in the copper furnace and embedded in the catalyst bed monitored the temperature. The pressure was regulated by back-pressure regulators and the flowrate of the gaseous reactant mixture was measure by soap bubble flowmeter.

Catalyst in the form of a fixed bed containing approximately 20 to 50 cm$^3$ of catalyst was used in the runs. The different catalysts were prepared from TiO$_2$ obtained in pure powder form from Degussa Company. It had a surface area of about 50 m$^2$/g. The powder was manually pelletized in a press and finally crushed and meshed to give particles of 60-120 mesh size range. Ruthenium was impregnated onto the meshed TiO$_2$ by means of depositing a ruthenium salt, e.g., RuCl$_3$ or Ru(NO$_3$)$_3$. The impregnation was carried out on the TiO$_2$ particles by stirring them in excess acetone containing dissolved Ru salt. Evaporation of acetone at room temperature caused deposition of the Ru salt on the TiO$_2$ solid which was allowed to dry at room temperature. The impregnated solid was reduced at 400°–450° C. for 2–4 hours under flowing H$_2$ atmosphere and was then ready for use before each run.

TABLE A

| Ru/TiO$_2$ Catalysts Used in the Examples | | | | |
|---|---|---|---|---|
| Catalyst | w/o Ru[a] | Salt Used | Volume[b] | Weight, g[c] |
| A | 0.76 | RuCl$_3$ | 50 | 43.7 |
| B | 0.93 | RuCl$_3$ | 30 | 29.9 |
| C | 1.10 | Ru(NO$_3$)$_3$ | 30 | 24.1 |

[a]Weight percent ruthenium, as the metal, in the catalyst.
[b]Volume of catalyst used in the reactor.
[c]Weight of catalyst used.

Hydrogen in the feedstream was passed through a Deoxo unit to remove traces of oxygen and then through a 4A molecular sieve trap to eliminate water vapor. Carbon monoxide (Matheson, ultrahigh purity) was also passed through a 4A molecular sieve trap prior to mixing with hydrogen in the feedstream.

The product stream exiting from the reactor contained light gases, liquid condensate and waxes and heavy hydrocarbons. The light gases were collected in a saturator and analyzed by a Carle Model AGC 311 gas chromatograph. Waxes and heavy hydrocarbons were collected in a container kept at about 90° C. and lighter condensate was collected in trapping vessels in a refrigerated water bath. The condensed products were analyzed chromatographically on a Perkin Elmer 900 or Sigma 2 gas chromatograph using generally either a 3 m. supported 20% SP 2100 column or a 2% SP 2100 column.

For each run, analysis of the reactor effluent gas stream was performed after the experiment had progressed for at least 10 hours. Condensed products were drained from the two trapping vessels only at the end of each experiment. After completing an experiment at a certain set of conditions and before another experiment was started, H$_2$ was passed over the catalyst overnight usually at the conditions of the completed experiment or at atmospheric pressure. The same catalyst sample could thus be used for a number of experiments.

EXAMPLE 1

Utilizing the general procedure and apparatus described hereinabove, three runs (Runs 1–3) using Catalyst A at an H$_2$/CO volume ratio of 2±0.1 and one run (Run 4) using Catalyst B and an H$_2$/CO molar ratio of 1.39, were made to determine the effect of temperature and pressure as reaction variables on the % CO conversion and the product slate. The reaction conditions and obtained results are listed below in Table I together with explanatory comments as footnotes.

TABLE I

| Process Variables and Product Distribution | Run Number | | | |
|---|---|---|---|---|
| | 1 | 2 | 3 | 4 |
| Pressure, (atm)[a] | 4.5 | 4.6 | 3.0 | 7.4 |
| Temp., °C. | 209 | 196 | 206 | 246 |
| GHSV, (v/v/hr.) | 215 | 210 | 198 | 172 |
| Run time, (hours)[b] | 39 (17) | 16.5 | 14.5 | 40 (24) |
| $H_2$ Conv., % | 94 | 86 | 84 | 90% |
| CO Conv., % | 99 | 86 | 84 | 71% |
| Product, wt. %[c] | | | | |
| $CH_4$ | 7.03 | 1.74 | 4.80 | 10.74 |
| $C_2$–$C_4$ | 6.97 | 5.44 | 9.15 | 19.40 |
| $C_5$–$C_{20}$[d] | 73.11 | 69.47 | 76.49 | 56.98 |
| $C_{21}$–$C_{40}$ | 10.20 | 17.69 | 8.28 | 9.53 |
| $C_{41}{}^+$[e] | 1.53 | 4.48 | 0.15 | 0.12 |
| Oxygenates[f] | 1.16 | 1.18 | 1.13 | 3.23 |

[a]Pressure values throughout the examples are in atmospheres absolute.
[b]Run time for each run indicates the total length of the run at a particular set of conditions. In most, but not all, cases it also indicates added time period for collection of indicated products. If the latter is different, it is given in parentheses next to the run time.
[c]The product wt. % data are presented on a $CO_2$-free basis, as a weight percentage of total hydrocarbons and oxygenates produced.
[d]The included $C_5$–$C_7$ wt. % values may be slightly low due to minor losses during liquid collection.
[e]Chromatographic analysis problems were found to exist for analyzing heavy $C_{41}{}^+$ product; thus the given $C_{41}{}^+$ data may be low in the range of about 10 to 40% of the value.
[f]Oxygenates, obtained in the water layer, were generally $C_1$–$C_5$ alcohols with methanol and ethanol being the major products.

As is seen in the above data, a substantial portion of the product slate in each run was comprised of the $C_5$–$C_{20}$ and $C_{21}$–$C_{40}$ hydrocarbon fractions. The higher temperature in Run 1 resulted in 99% CO conversion as compared to the lower temperature of Run 2. However, Run 2 exhibited a lower methane make and also a slightly heavier hydrocarbon make.

A decrease in the pressure in Run 3 as contrasted to Run 1 resulted in a lower % CO conversion and lower methane make. This points to a general rule in the process that lower temperatures and pressures tend to lower % CO conversions and methane makes, while lower temperatures tend to lead slightly heavier hydrocarbon make.

EXAMPLE 2

Utilizing the same general procedure and apparatus described in Example 1, the following runs were made utilizing Catalyst A and an $H_2$/CO ratio of about 2 to further demonstrate the influence of temperature and pressure on % CO conversion and product slate. The results and conditions of each run are tabulated below in Table II. The explanatory comments for Table I in Example 1 are also applicable and incorporated herein.

TABLE II

| Process Variables and Product Distribution | Run Number | | |
|---|---|---|---|
| | 5 | 6 | 7 |
| Pressure, (atm) | 3.0 | 5.0 | 5.0 |
| Temp., °C. | 224 | 203 | 218 |
| GHSV, (v/v/hr.) | 301 | 298 | 494 |
| Run Time, (hours) | 17.5 | 17.0 | 18.5 |
| $H_2$ Conv., % | 84 | 87 | 89 |
| CO Conv., % | 84 | 85 | 89 |
| Product, wt. % | | | |
| $CH_4$ | 6.14 | 2.51 | 5.38 |
| $C_2$–$C_4$ | 11.59 | 5.42 | 7.91 |
| $C_5$–$C_{20}$ | 74.45 | 65.62 | 72.69 |
| $C_{21}$–$C_{40}$ | 6.24 | 20.02 | 11.29 |
| $C_{41}{}^+$ | 0.13 | 5.48 | 1.49 |

TABLE II-continued

| Process Variables and Product Distribution | Run Number | | |
|---|---|---|---|
| | 5 | 6 | 7 |
| Oxygenates | 1.45 | 0.95 | 1.24 |

As is seen from the data, in order to obtain a % CO conversion in Run 5 equivalent to that in Run 3 (Example 1) at lower space velocity but at the same pressure, the temperature had to be increased from 206° to 224° C.

Increasing the GHSV to 494 v/v/hr. in Run 7, but keeping the pressure at 5 atm. as in Run 6, in addition to raising the temperature to 218° C., resulted in CO conversion of 89%.

EXAMPLE 3

Utilizing the general procedure and apparatus described in Example 1, the following runs were made utilizing Catalyst B and an $H_2$/CO volume ratio of about 2, to illustrate reproducibility of the process, and to examine the effect of different pressures and temperatures. Results and conditions of the runs are given below in Table III. The explanatory comments of Example 1 are also applicable.

TABLE III

| Process Variables and Product Distribution | Run Number[a] | | | | |
|---|---|---|---|---|---|
| | 8 | 9 | 10 | 11 | 12 |
| Pressure, (atm) | 2.5 | 5.35 | 2.78 | 6.2 | 2.78 |
| Temp., °C. | 225 | 203 | 224 | 193 | 225 |
| GHSV, (v/v/hr.) | 299 | 298 | 304 | 298 | 322 |
| Run time, (hours) | 18.5 (6.5) | 14.5 | 19 (7) | 14 | 40 (7.5) |
| $H_2$ Conv., % | 86 | 83 | 86 | 81 | 85 |
| CO Conv., % | 85 | 82 | 84 | 81 | 82 |
| Product, wt. % | | | | | |
| $CH_4$ | 9.21 | 4.26 | 8.79 | 3.10 | 10.21 |
| $C_2$–$C_4$ | 19.48 | 11.54 | 18.13 | 9.20 | 18.87 |
| $C_5$–$C_{20}$ | 61.37 | 68.66 | 63.98 | 70.30 | 61.79 |
| $C_{21}$–$C_{40}$ | 7.46 | 11.15 | 6.76 | 11.86 | 6.77 |
| $C_{41}{}^+$ | 0 | 1.58 | 0 | 2.20 | 0 |
| Oxygenates | 2.48 | 2.81 | 2.34 | 3.34 | 2.36 |

[a]Catalyst B was used in these runs (0.93 w/o Ru/$TiO_2$).

As is seen from the data, the high pressures used in Runs 9 and 11 yielded slightly higher $C_5$–$C_{20}$ fractions. Reproducibility of the process was good as indicated by the % CO and % $H_2$ conversions, and product make for Runs 8, 10 and 12.

EXAMPLE 4

Utilizing the general procedure and apparatus described in Example 1, the following runs were made to see the effect of different space velocities on the process. The results are tabulated below in Table IV which also includes the comments of Example 1.

TABLE IV

| Process Variables and Product Distribution | Run Number[a] | | | |
|---|---|---|---|---|
| | 13 | 14 | 15[b] | 16[b] |
| Pressure, (atm) | 4.2 | 4.3 | 5 | 5.1 |
| Temp., °C. | 213 | 213 | 205 | 204 |
| GHSV, (v/v/hr.) | 301 | 1240 | 305 | 1506 |
| Run time, (hours) | 40 (28) | 36 (24) | 19.5 | 24 |
| $H_2$ Conv., % | 87 | 26 | 94 | 23 |
| CO conv., % | 85 | 30 | 99 | 20 |
| Product, wt. % | | | | |
| $CH_4$ | 6.38 | 6.88 | 5.39 | 5.21 |

TABLE IV-continued

| Process Variables and Product Distribution | Run Number[a] | | | |
|---|---|---|---|---|
| | 13 | 14 | 15[b] | 16[b] |
| $C_2$-$C_4$ | 13.09 | 17.84 | 10.30 | 20.70 |
| $C_5$-$C_{20}$ | 66.89 | 64.08 | 75.18 | 65.97 |
| $C_{21}$-$C_{40}$ | 10.02 | 8.35 | 6.75 | 5.62 |
| $C_{41}{}^+$ | 0.49 | 0.18 | 0.33 | 0.15 |
| Oxygenates | 3.13 | 2.67 | 2.05 | 2.35 |

[a]Catalyst B was used (0.93 w/o Ru/TiO$_2$).
[b]Catalyst containing 0.92 w/o Ru/TiO$_2$ made similarly to Catalyst C was used.

As seen from the data, an increase in the space velocity, as in Runs 14 and 16, had a significant reduction on the % CO conversion.

The product streams from Example 4 was also analyzed for the presence of alpha-olefins and internal olefins. The data are tabulated below in Tables V and Va. The explanatory comments of Example 1 are applicable. The weight percentage of olefins noted herein, were estimated from chromatographic data and may be in error of about 15-20% due to small uncertainties in extrapolation.

TABLE V

| Process Variables and Product Distribution | Run Number | | | |
|---|---|---|---|---|
| | 13 | 14 | 15 | 16 |
| GHSV, (v/v/hr.) | 301 | 1240 | 305 | 1506 |
| w/o $C_2H_4$ in $C_2$ cut[a] | 5 | 40 | 1 | 45 |
| w/o $C_3H_6$ in $C_3$ cut[a] | 67 | 84 | 21 | 80 |
| w/o 1-$C_4H_8$/2-$C_4H_8$ in $C_4$ cut[a] | 37/27 | 66/16 | 6/32 | 54/24 |
| Total olefin in $C_7$-$C_{12}$ cut[a] | 25 | 39 | — | — |
| Total olefin in $C_5$-$C_{20}$ cut[a] | 21 | 31 | 11 | 36 |

TABLE VA

| Olefin breakdown, %[a] | Run Number | | | |
|---|---|---|---|---|
| | 13 | | 14 | |
| | alpha | internal | alpha | internal |
| $C_7$ | 8 | 27 | 52 | 10 |
| $C_8$ | 5 | 25 | 43 | 10 |
| $C_9$ | 4 | 22 | 35 | 11 |
| $C_{10}$ | 3.5 | 17 | 25 | 9 |
| $C_{11}$ | 3.7 | 12 | 18 | 8 |
| $C_{12}$ | 3.7 | 9 | 13 | 7 |

[a]Rest of product mostly n-paraffins.

As is seen from the data, the products produced from Ru/TiO$_2$ are mainly n-paraffins and some olefins. Increasing the space velocity tends to increase the alpha-olefins content and the olefin percentage tends to decrease rapidly with increasing carbon number.

EXAMPLE 5

Utilizing the apparatus and general procedure described in Example 1, the following runs were conducted to determine if the catalyst could be run at high space velocities with 80% CO conversion. Results are tabulated below in Table VI. The comments of Example 1 are incorporated herein.

TABLE VI

| Process Variables and Product Distribution | Run Number[a] | | | |
|---|---|---|---|---|
| | 17 | 18 | 19 | 20[b] |
| Pressure, (atm) | 12.0 | 19.8 | 21.0 | 23.0 |
| Temp., °C. | 209 | 207 | 207 | 211 |
| GHSV, (v/v/hr.) | 780 | 1280 | 1240 | 2020 |
| Run time, (hours) | 13.5 | 29 | 18 | — |
| $H_2$ Conv., % | 84 | 94 | 85 | 53 |
| CO Conv., % | 79 | 87 | 79 | 53 |
| Products, wt. % | | | | |
| $CH_4$ | 4.51 | 5.19 | 5.09 | 5.5 |
| $C_2$-$C_4$ | 10.17 | 6.41 | 8.49 | 8.8 |
| $C_5$-$C_{20}$ | 57.79 | 51.63 | 54.07 | 61.6 |
| $C_{21}$-$C_{40}$ | 17.26 | 26.24 | 23.42 | 17.3 |
| $C_{41}{}^+$ | 8.70 | 9.44 | 7.75 | 4.7 |
| Oxygenates | 1.57 | 1.09 | 1.18 | 2.1 |

[a]Catalyst C (1.1 w/o Ru/TiO$_2$).
[b]$C_5$-$C_{20}$ olefins content was 26 weight percent, remainder being paraffins. A different batch of Catalyst C was used, containing 1.05 w/o Ru/TiO$_2$.

As is seen from the data, higher space velocities should be coupled with higher pressures in order to maintain high % CO conversions.

EXAMPLE 6

Utilizing the general procedure and apparatus described in Example 1, the followng runs were made to determine the effect of Ru/Nb$_2$O$_5$, Ru/Ta$_2$O$_5$ and Ru/SiO$_2$ catalysts on the process as versus Ru/TiO$_2$. The results are tabulated below in Table VII. The comments of Example 1 are incorporated herein.

TABLE VII

Effect of Supports on Product Selectivity

| Process Variables and Product Distribution | Catalyst | | | |
|---|---|---|---|---|
| | 0.76% Ru/TiO$_2$ | 0.56% Ru/Nb$_2$O$_5$[b] | 0.67% Ru/Ta$_2$O$_5$[c] | 1.57% Ru/SiO$_2$[d] |
| Pressure, (atm.)[a] | 5 | 5 | 5.2 | 21 | 31 |
| Temp., °C. | 203 | 196 | 200 | 251 | 245 |
| GHSV, (v/v/hr.) | 298 | 300 | 303 | 200 | 199 |
| $H_2$ + CO Conv., % | 86 | 88.3 | 79 | 88.7 | 89.8 |
| Selectivity — Hydrocarbon, wt. % | | | | | |
| $CH_4$ | 2.9 | 2.0 | 5.5 | 7.5 | 5.6 |
| $C_2$-$C_4$ | 6.2 | 2.5 | 18.5 | 17.4 | 11.6 |
| $C_5$-$C_{20}$ | 65.5 | 62.1 | 66.5 | 71.3 | 74.9 |
| $C_{21}{}^+$ | 25.4 | 33.4 | 9.5 | 3.8 | 7.9 |

[a]$H_2$CO ratio was about 2.
[b]Catalyst was prepared in same manner as described herein for corresponding TiO$_2$ support, except Nb$_2$O$_5$ was employed.
[c]Catalyst was prepared in same manner as described herein for TiO$_2$ support, except Ta$_2$O$_5$ was employed.
[d]Catalyst was prepared in same manner as described herein for TiO$_2$ support, except SiO$_2$ was employed.

In order to compare the relative activities and product selectivities of the catalysts, the process conditions had to be adjusted to approximately equal % CO conversion. As is seen, the run for Ru/SiO$_2$ had to be adjusted to higher pressure, higher temperature and lower space velocity to achieve the same % CO conversion, indicating a higher catalyst activity for Ru/TiO$_2$, Ru/Ta$_2$O$_5$ and Ru/Nb$_2$O$_5$ as compared to Ru/SiO$_2$.

EXAMPLE 7

Utilizing the general procedure and apparatus described in Example 1, the following runs were made to further compare the activity of Ru/Nb$_2$O$_5$ versus Ru/SiO$_2$ as catalysts in the process.

TABLE VIII

Comparison of the Activity of Ru/Nb$_2$O$_5$ and Ru/SiO$_2$
H$_2$/CO = 2

| Process Variables and Product Distribution | Catalyst | |
|---|---|---|
| | 0.56% Ru/Nb$_2$O$_5$ | 1.57% Ru/SiO$_2$ |
| Pressure, (atm.) | 7 | 21 |
| Temp., °C. | 229 | 251 |
| Space vel., (v/v/hr.) | 1225 | 990 |
| H$_2$ + CO Conv., % | 81 | 15 |

As is seen from the data, increasing the space velocity of both runs, as compared to Example 7 with slight adjustments for pressure and temperature, resulted in a dramatic decrease in % CO conversion for the Ru/SiO$_2$ catalyst as compared to Ru/Nb$_2$O$_5$.

EXAMPLE 8

Utilizing the general process and apparatus described in Example 1, the following runs were made to further compare the activity of Ru/TiO$_2$ versus Ru/SiO$_2$ as catalysts in the process. Results are tabulated below in Table IX.

TABLE IX

TiO$_2$ vs. SiO$_2$ as Catalyst Support
P = 4.6 atm., H$_2$/CO = 2, GHSV 300 v/v/hr.

| Process Variables and Product Distribution | Catalyst | | |
|---|---|---|---|
| | 1.1% Ru/TiO$_2$ | 1.6% Ru/SiO$_2$ | |
| Temp., °C. | 209 | 209 | 323 |
| H$_2$+ CO Conv., % | 82 | 5 | 71 |
| N$_{CO}$* × 10$^3$, s$^{-1}$ | 10.6 | 1.1 | 13.9 |
| Selectivity — % CO Conv. to: | | | |
| CO$_2$ | 1.6 | 4.3 | 11.7 |
| CH$_4$ | 4.3 | 10.6 | 60.1 |
| C$_2$ | 1.1 | 5.3 | 9.8 |
| C$_3$-C$_4$ | 11.4 | 28.7 | 8.6 |
| C$_5$+ | 81.6 | 51.1 | 9.8 |

N$_{CO}$* = Turnover frequency with respect to total Ru.

As is seen from the data, under similar conditions, Ru/TiO$_2$ gave 82% conversion, as compared to only 5% for Ru/SiO$_2$. Increasing the temperature in the case of the Ru/SiO$_2$ run, increased the % CO conversion to 71%, but with attendant high methane make.

EXAMPLE 9

Utilizing the general procedure and apparatus described in Example 11, the following runs were made to determine the effect of pressure on the activity of Ru/TiO$_2$ and Ru/SiO$_2$ catalysts. The results are tabulated below in Table X.

TABLE X

Effect of Pressure on Activity
H$_2$/CO = 2, T = 209° C.

| Process Variables | Catalyst | | | |
|---|---|---|---|---|
| | 1.1% Ru/TiO$_2$ | | 1.6% Ru/SiO$_2$ | |
| Pressure, (atm.) | 4.6 | 21 | 4.6 | 21 |
| GHSV, (v/v/hr.) | 300 | 1240 | 300 | 274 |

TABLE X-continued

Effect of Pressure on Activity
H$_2$/CO = 2, T = 209° C.

| Process Variables | Catalyst | | | |
|---|---|---|---|---|
| | 1.1% Ru/TiO$_2$ | | 1.6% Ru/SiO$_2$ | |
| H$_2$+ CO conv., % | 82 | 83 | 5 | 5 |

As seen from the data, the activity of Ru/TiO$_2$ catalyst is greater even at higher space velocities than the corrresponding Ru/SiO$_2$ catalyst.

EXAMPLE 10

Utilizing the general procedure and apparatus described in Example 9, the following runs were made as a comparison between similar ruthenium loadings on TiO$_2$ and gamma Al$_2$O$_3$. Results are tabulated below in Table XI. As is seen, Ru/TiO$_2$ is more active and makes less CH$_4$ and C$_2$-C$_4$ hydrocarbons, and more C$_5$+ hydrocarbons than Ru/Al$_2$O$_3$.

TABLE XI

| Process Variables[a] | 1.1 w/o Ru/TiO$_2$ | 1.1 w/o Ru/AL$_2$O$_3$ |
|---|---|---|
| H$_2$ + CO Conv. % | 87 | 32 |
| N$_{CO}$* × 10$^3$, s$^{-1}$ | 9.5 | 3.7 |
| Products, w/o | | |
| CH$_4$ | 6.7 | 16.6 |
| C$_2$-C$_4$ | 12.8 | 19.5 |
| C$_5$-C$_{20}$ | 68.8 | 59.2 |
| C$_{21}$+ | 9.2 | 2.9 |
| Oxygenates | 2.5 | 1.8 |

[a] Pressure = 2.1 atm., Temp. = 214° C., GHSV = 303 v/v/hr., H$_2$/CO = 2.

What is claimed is:

1. A process for selectively producing paraffins comprising:
   (a) first contacting a mixture of H$_2$ and CO for at least 10 hours with a reduced and supported ruthenium catalyst, said ruthenium catalyst comprising ruthenium on a support selected from the group consisting of TiO$_2$, ZrTiO$_4$, TiO$_2$-carbon, TiO$_2$-Al$_2$O$_3$, TiO$_2$-SiO$_2$, alkaline earth titanates, alkali titanates, rare earth titanates, V$_2$O$_3$, Nb$_2$O$_5$, Ta$_2$O$_5$, Al$_2$O$_3$-V$_2$O$_3$, Al$_2$O$_3$-Nb$_2$O$_5$, Al$_2$O$_3$-Ta$_2$O$_5$, SiO$_2$-V$_2$O$_3$, SiO$_2$-Nb$_2$O$_5$, SiO$_2$-Ta$_2$O$_5$, V$_2$O$_3$-carbon, Nb$_2$O$_5$-carbon, Ta$_2$O$_5$-carbon, alkaline earth Group VB oxides, alkali-Group VB oxides, rare earth-Group VB oxides, Group IVB-Group VB oxides, and mixtures thereof, at Fischer-Tropsch conditions such that the temperature ranges from about 100° to 400° C., the pressure ranges from about 0.2 to 10 MPaA, the gas hourly space velocity, GHSV, ranges from about 100 to 50,000 v/v/hr., and wherein the ratio of GHSV/pressure is below about 24,000 v/v/hr./MPaA, and at least about a 20% CO conversion is effected; and
   (b) continuing said contacting as in step (a) at a H$_2$/CO molar ratio from about 0.1 to 4 and thereafter recovering a hydrocarbon mixture comprising C$_5$-C$_{40}$ hydrocarbons, containing C$_5$-C$_{20}$ paraffins and olefins in a paraffins to olefins weight ratio of at least about 1.5.

2. The process of claim 1 wherein the ruthenium concentration in said catalyst is from 0.01 to 15 percent by weight.

3. The process of claim 1 wherein said ruthenium concentration is from 0.1 to 5 percent by weight.

4. The process of claim 1 wherein said catalyst is selected from $Ru/TiO_2$, $Ru/Nb_2O_5$, $Ru/V_2O_3$, $Ru/Ta_2O_5$, or mixtures thereof.

5. The process of claim 4 wherein said catalyst is $Ru/TiO_2$.

6. The process of claim 1 wherein said percent CO conversion is 50 percent and higher.

7. The process of claim 1 wherein said $C_5$-$C_{40}$ hydrocarbon products comprise about 60 weight percent of total hydrocarbons produced.

8. The process of claim 1 wherein said $C_5$-$C_{40}$ hydrocarbon products comprise $C_5$-$C_{20}$ paraffins and olefins in a paraffins to olefins weight ratio of 1.8 and higher.

9. The process of claim 1 wherein total hydrocarbon products further comprise up to about 15 weight percent methane.

10. The process of claim 9 wherein said total hydrocarbon products further comprise up to about 10 weight percent methane.

11. The process of claim 1 wherein said temperature is in the range of 150° to 300° C.

12. The process of claim 1 wherein said pressure is in the range of 0.2 to 5.0 MPaA.

13. The process of claim 1 wherein said GHSV is in the range of 100 to 5000 v/v/hr.

14. The process of claim 1 wherein said $H_2/CO$ molar ratio is from 1 to 3.

15. A process for selectively producing paraffins comprising (a) first contacting a mixture of $H_2$ and CO for at least 10 hours with a reduced and supported $Ru/TiO_2$ catalyst, wherein the concentration of ruthenium in the catalyst is 0.1 to 5 weight percent, at Fischer-Tropsch conditions such that the temperature ranges from 150° to 300° C., the pressure ranges from 0.2 to 5 MPaA, the gas hourly space velocity, GHSV, ranges from 100 to 5000 v/v/hr., GHSV/pressure is below about 24,000 v/v/hr./MPaA, the $H_2$ to CO molar ratio ranges from 1 to 3 and the percent CO conversion is about 50 percent and higher; and (b) continuing said contacting as in step (a) and thereafter recovering a hydrocarbon mixture comprising $C_5$-$C_{40}$ hydrocarbons containing $C_5$-$C_{20}$ paraffins and olefins in a paraffins to olefins weight ratio of about 1.8 and higher.

* * * * *